United States Patent [19]

Michalczyk et al.

[11] Patent Number: 5,684,111

[45] Date of Patent: Nov. 4, 1997

[54] SILYLATED DIOXOLANE POLYMERS AND MONOMERIC COMPOUNDS

[75] Inventors: Michael Joseph Michalczyk; Ming-Hong Hung; Lech Wilczek, all of Wilmington, Del.

[73] Assignee: E. I. Du Pont de Nemours and Company, Wilmington, Del.

[21] Appl. No.: 683,514

[22] Filed: Jun. 14, 1996

Related U.S. Application Data

[60] Provisional application No. 60/000,591, Jun. 28, 1995.

[51] Int. Cl.[6] ................................................ C08G 77/04
[52] U.S. Cl. ........................... 528/27; 528/15; 528/31; 549/214
[58] Field of Search ........................ 528/27, 15, 31; 549/214

[56] References Cited

U.S. PATENT DOCUMENTS

| | | | |
|---|---|---|---|
| 3,865,845 | 2/1975 | Resnick | 260/340.9 |
| 5,233,058 | 8/1993 | Anton et al. | 549/450 |
| 5,233,071 | 8/1993 | Wilczek | 556/479 |
| 5,286,825 | 2/1994 | Anton et al. | 526/247 |

*Primary Examiner*—Margaret W. Glass

[57] ABSTRACT

This invention relates to novel polymeric and monomeric silane substituted fluorinated 1,3-dioxolane compounds and their preparation from 4,5-difluoro-1,3-dioxolane and difunctional or monofunctional silicon hydrides.

18 Claims, No Drawings

SILYLATED DIOXOLANE POLYMERS AND MONOMERIC COMPOUNDS

This application claims the priority benefit of U.S. Provisional Application 60/000,591, filed Jun. 28, 1995.

FIELD OF THE INVENTION

This invention relates to dioxolane polymers and compounds and in particular concerns certain novel dioxolane polymers and compounds prepared from 4,5-difluoro-4,5-divinyl-1,3-dioxolanes.

TECHNICAL BACKGROUND

U.S. Pat. Nos. 5,233,058 and 5,286,825, Anton et al. discloses 2,2-bis(trifluoromethyl)-4,5-difluoro-4,5-divinyl-1,3-dioxolane compounds having the formula

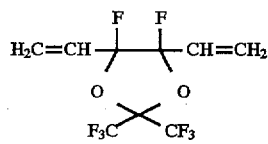

and copolymers of this compound with tetrafluoroethylene.

U.S. Pat. No. 5,233,071, Wilczek, discloses a process for the hydrosilylation of alpha fluorinated olefins having the formula $H_2C=CHCFR^aR^b$ where $R^a$ is fluorine or perfluorohydrocarbyl and $R^b$ is fluorine, hydrogen, hydrocarbyl or substituted hydrocarbyl in the presence of a catalytically effective amount of a cobalt catalyst of the formula $Co_2(CO)_{8-x}L_x$.

Applicants have found that certain novel silylated dioxolane compounds prepared from compounds such as those disclosed in U.S. Pat. No. 5,286,825 are particularly useful as additives to polymers, and as primers, surface modifying agents and lubricants.

SUMMARY OF THE INVENTION

This invention provides a polymer comprising repeat units of formula I

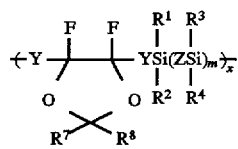

wherein:

x is an integer from 2 to 100;

m is an integer from 1 to 50;

$R^1$, $R^2$, $R^3$ and $R^4$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, oxysilyl or hydrogen;

Z is a divalent group selected from O, S, $R^6N$;

$R^6$ is $C_1$ to about $C_8$ alkyl;

$R^7$ and $R^8$ are each independently $C_1$ to $C_8$ fluoroalkyl or fluorine;

Y is $(CR^9R^{10})_kCR^{11}HCR^{13}R^{14}$;

$R^9$, $R^{10}$, $R^{11}$, $R^{13}$ and $R^{14}$ are each independently hydrogen, $C_1$ to about $C_8$ alkyl, or aryl; and k is an integer from 0 to 10.

This invention also provides a process for the preparation of a polymer comprising repeat units of formula I

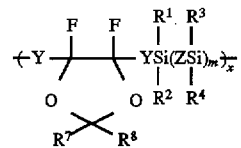

wherein:

x is an integer from 2 to 100;

m is an integer from 1 to 50;

$R^1$, $R^2$, $R^3$ and $R^4$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, oxysilyl or hydrogen;

Z is a divalent group selected from O, S, $R^6N$;

$R^6$ is $C_1$ to about $C_8$ alkyl;

$R^7$ and $R^8$ are each independently $C_1$ to $C_8$ fluoroalkyl or fluorine;

Y is $(CR^9R^{10})_kCR^{11}HCR^{13}R^{14}$;

$R^9$, $R^{10}$, $R^{11}$, $R^{13}$ and $R^{14}$ are each independently hydrogen, $C_1$ to about $C_8$ alkyl, or aryl; and k is an integer from 0 to 10 comprising contacting a silicon hydride of formula II

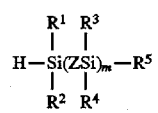

wherein $R^5$ is $C_1$ to $C_{20}$ alkyl, aryl, vinyl or hydrogen and m, Z, $R^1$, $R^2$, $R^3$ and $R^4$ are as defined for formula I, with a divinyl dioxolane of formula III

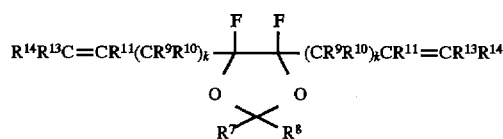

wherein $R^7$, $R^8$, $R^9$, $R^{10}$, $R^{11}$, $R^{13}$, $R^{14}$ and k are as defined for formula I, in the presence of a transition metal catalyst to form a polymer comprising repeat units of formula I.

This invention further provides a compound of formula IA

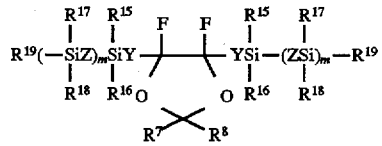

wherein:

m is an integer for 0 to 50;

$R^{15}$, $R^{16}$, $R^{17}$ and $R^{18}$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, $C_1$ to $C_{14}$ fluorocarboxy, oxysilyl or hydrogen;

$R^{19}$ is $C_1$ to $C_{20}$ alkyl, aryl, $C_1$ to $C_{20}$ alkoxy, $C_2$ to $C_{20}$ fluoroalkoxy, $C_1$ to $C_{20}$ carboxy, $C_1$ to $C_{14}$ fluorocarboxy, halogen, vinyl or hydrogen;

Z is a divalent group selected from O, S, $R^6N$;

$R^6$ is $C_1$ to about $C_8$ alkyl;

$R^7$ and $R^8$ are each independently $C_1$ to $C_8$ fluoroalkyl or fluorine;

Y is $(CR^9R^{10})_kCR^{11}HCR^{13}R^{14}$;

$R^9$, $R^{10}$, $R^{11}$, $R^{13}$ and $R^{14}$ are each independently hydrogen, $C_1$ to about $C_8$ alkyl or aryl; and k is an integer from 0 to 10.

This invention also provides a process for preparing a compound of formula IA

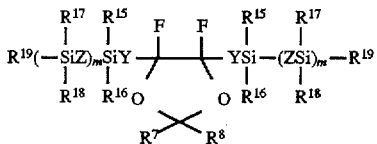

wherein:

m is an integer for 0 to 50;

$R^{15}$, $R^{16}$, $R^{17}$ and $R^{18}$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, $C_1$ to $C_{14}$ fluorocarboxy, oxysilyl or hydrogen;

$R^{19}$ is $C_1$ to $C_{20}$ alkyl, aryl, $C_1$ to $C_{20}$ alkoxy, $C_2$ to $C_{20}$ fluoroalkoxy, $C_1$ to $C_{20}$ carboxy, $C_1$ to $C_{14}$ fluorocarboxy, halogen, vinyl or hydrogen;

Z is a divalent group selected from O, S, $R^6$N;

$R^6$ is $C_1$ to about $C_8$ alkyl;

$R^7$ and $R^8$ are each independently $C_1$ to $C_8$ fluoroalkyl or fluorine;

Y is $(CR^9R^{10})_kCR^{11}HCR^{13}R^{14}$;

$R^9$, $R^{10}$, $R^{11}$, $R^{13}$ and $R^{14}$ are each independently hydrogen, $C_1$ to about $C_8$ alkyl or aryl; and k is an integer from 0 to 10, comprising: contacting a silicon hydride of formula IIA

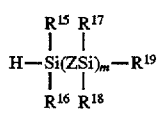

wherein m, Z, $R^{15}$, $R^{16}$, $R^{17}$, $R^{18}$ and $R^{19}$ are as defined for formula IA, with a divinyl dioxolane of formula III

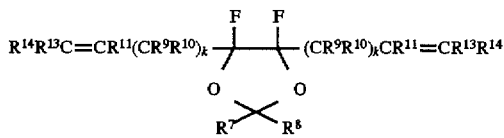

wherein $R^7$, $R^8$, $R^9$, $R^{10}$, $R^{11}$, $R^{13}$, $R^{14}$ and k are as defined for formula IA, in the presence of a transition metal catalyst to form a compound of formula IA.

DETAILED DESCRIPTION OF THE INVENTION

The present invention concerns polymeric silane substituted fluorinated 1,3-dioxolanes of formula I and monomeric silane substituted fluorinated 1,3-dioxolanes of formula IA.

For the polymers and monomeric compounds of the present invention and products of the processes of the present invention, Y is $(CR^9R^{10})_kCR^{11}HCR^{13}R^{14}$. Preferably, $R^9$, $R^{10}$, $R^{11}$, $R^{13}$ and $R^{14}$ are hydrogen and k=0 or 1. x is an integer from 2 to 100; preferably 2 to 20 for formula I. m is an integer from 1 to 50 for the polymer and 0 to 50 for the monomer. Preferably m is less than or equal to 10, most preferably, less than or equal to 3. Preferably $R^1$, $R^2$, $R^3$, $R^4$ and $R^5$ are $C_1$ to $C_4$ alkyl, $C_1$ to $C_4$ alkoxy, $C_2$ to $C_4$ fluoroalkoxy, chlorine or hydrogen. Preferably $R^{15}$, $R^{16}$, $R^{17}$, $R^{18}$ and $R^{19}$ are $C_1$ to $C_4$ alkyl or alkoxy, aryl, $C_2$ to $C_4$ fluoroalkoxy, $C_2$ to $C_4$ fluorocarboxy, $C_1$ to $C_6$ acyloxy, bromine or chlorine. A preferred aryl group is phenyl; preferred fluoroalkoxy are $CF_3CH_2O$, $C_2F_5CH_2O$, $C_3F_7CH_2O$; a preferred fluorocarboxy is $CF_3COO$; preferred acyloxy are HCOO and $CH_3COO$; and a preferred aryloxy group is phenoxy. Preferably, Z is O; $R^6$ is preferably $CH_3$ or $CH_2CH_3$, and $R^7$ and $R^8$ are preferably both $CF_3$.

The polymers and monomeric compounds of the present invention are formed by contacting the divinyl dioxolane of formula III with the silicon hydride of formula II or IIA in the presence of a transition metal catalyst. Preferred transition metal catalysts include Pt, $Co_2(CO)_8$ and $Co_2(CO)_{8-z}L_z$ wherein z is 0 or an integer of 1 to 7; each L is independently CO, $PR^{20}_3$ or $P(OR^{21})_3$; $R^{20}$ is hydrocarbyl; $R^{21}$ is hydrocarbyl; and provided that when L is $PR^{20}_3$ only one or two of $R^{20}$ is aryl. A preferred hydrocarbyl group is methyl. A most preferred catalyst for preparing compounds of formula IA is Pt and the most preferred catalyst for preparing a polymer comprising repeat units of formula I is $Co_2(CO)_8$.

By a "silicon hydride" is meant a compound that contains one or more hydrogen atoms bound directly to silicon (Si—H). The silicon hydride can have only one hydrogen atom bound to a silicon atom, can have more than one hydrogen bound to any particular silicon atom, and/or can have more than one silicon atom that has hydrogen bound to it. Any other group that is substantially stable during the process of the present invention can be bound to the silicon, such as hydrocarbyl, including alkyl, aryl, and cycloalkyl; substituted hydrocarbyl; halogen including chlorine, bromine and fluorine; alkoxy; fluoroalkoxy; aryloxy; acyloxy; fluorocarboxy and oxysilyl (to form a siloxane group). Many such compounds are commercially available.

One preferred silicon hydride of formula II is $R_aSiH_{4-a}$ wherein each R is independently alkyl containing 1 to 4 carbon atoms; aryl; chlorine; bromine; alkoxy containing 1 to 4 carbon atoms, including fluorine substituted alkoxy groups; $C_1$ to $C_4$ fluorocarboxy and acyloxy containing 1 to 6 carbon atoms, and a is 1, 2 or 3. In an especially preferred silicon hydride, each R is independently methyl, ethyl, phenyl, methoxy, ethoxy, trifluoroaceloxy, aceloxy, formyl, 2,2,2 trifluoroethoxy, n-heptafluorobutoxy or chloro.

Another preferred silicon hydride is $R_bH_{3-b}SiOSiR_bH_{3-b}$ wherein R is as defined above and b is 0, 1, or 2. Especially preferred R groups are as given above.

Another preferred silicon hydride is a cyclic siloxane of the formula $(R_2SiO)_v(R_tH_{2-t}SiO)y$, wherein R is as defined above, v+y is 3, 4, or 5, y is an integer of one or more, v is 0, 1, 2, 3 or 4, and t is 0 or 1. Especially preferred R groups are as defined above.

Another preferred silicon hydride is a linear polysiloxane of the formula $R_3SiO(R_2SiO)_q(R_sH_{2-s}SiO)_rSiR_3$, wherein R is as defined above, q is 0 or an integer of 1 or more, r is an integer of 1 or more, and each s is independently 0 or 1. Especially preferred R groups are as given above. In preferred linear polysiloxanes q+r is about 5 to about 10,000, and it is more preferred if q+r is about 10 to about 1,000. For the linear polysiloxanes, it is more preferred if each R is methyl, ethyl or phenyl, and most preferred if each R is methyl.

Difunctional silanes, i.e., silanes possessing more than one hydrogen capable of reacting, preferred in the practice of this invention include 1,1,3,3-tetramethyldisiloxane; 1,3-diphenyl-1,3-dimethyldisiloxane; $HSi(CH_3)_2OSi(CH_3)_2OSi(CH_3)_2H$; and $HSi(CH_3)(OSi(CH_3)_3)OSi(CH_3)(OSi(CH_3)_3)H$.

If the compound of formula IIA is monofunctional, i.e., has one hydrogen atom (none of $R^{15}$, $R^{16}$, $R^{17}$, $R^{18}$ or $R^{19}$ are H), the process of the present invention is carried out by contacting at least one monofunctional compound of formula IIA with at least one compound of formula III in the presence of a catalytic amount of a metal transition catalyst in an optional solvent, such as tetrahydrofuran, a fluorocarbon or toluene, at a temperature ranging from about 25° C. to about 120° C. for a time sufficient for a compound of formula IA to be generated. The resultant solution comprising the compound of formula IA can be cooled and volatiles removed, for example in vacuo to isolate the compound of formula IA.

If the $R^{15}$ to $R^{19}$ groups of the monofunctional compound of formula IIA are halogen, then the result of the reaction described above is a halosilane of formula IA. A further step can be used to generate a second compound of formula IA. To a solution comprising the halosilane is added an alcohol or a fluoroalcohol, such as $CH_3CH_2OH$, $CF_3CH_2OH$ or n-$C_3F_7CH_2OH$. The solution is optionally heated and during the subsequent reaction, gas, such as HCl if chlorosilane is used, can be vented off by bubbling an inert gas such as argon through the solution. After cooling, the second compound of formula IA can be isolated by removal of the volatiles.

The following diagram outlines embodiments of the present invention for certain monofunctional silicon hydrides.

hydrogen, but only one reacts for steric, electronic or other reasons, again, 2:1 adducts are obtained. The compounds of formula IA generated from monofunctional silicon hydrides wherein m is 0 are preferred.

Representative examples of preferred 2:1 adducts of formula IA are 2,2-bis(trifluoromethyl)-4,5-difluoro-4,5 bis(trichlorosilylethyl)-1,3-dioxolane; 2,2-bis(trifluoromethyl)-4,5-difluoro-4,5 bis(triethoxysilylethyl)-1,3-dioxolane; 2,2-bis(trifluoromethyl)-4,5-difluoro-4,5 bis(tris(2,2,-trifluoroethoxy)silylethyl)-1,3-dioxolane; and 2,2-bis(trifluoromethyl)-4,5-difluoro-4,5 bis(tris(1H,1H-heptafluorobutoxy)silylethyl)-1,3-dioxolane.

If the compound of formula II is difunctional, the process of the present invention is afforded by contacting at least one compound of formula II with at least one compound of formula III in the presence of a catalytically effective amount of a metal transition catalyst. After allowing sufficient time for the reactions to occur, a compound of formula I is generated.

If difunctional silanes are employed, the products comprise oligomeric or polymeric materials, i.e., x is an integer greater than 1.

Hydrosilylation of difunctional silicon hydrides give fluorine-bearing dioxolane and siloxane polymers containing fluorinated dioxolane and siloxane segments, as shown

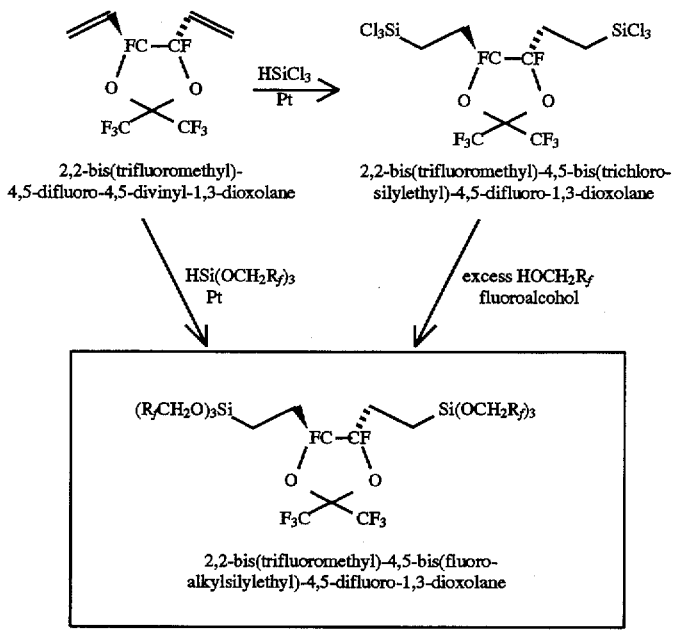

If the silicon hydride of formula IIA is mono-functional, the products are 2:1 silane to dioxolane adducts, i.e., compounds of formula IA. If the silanes have more than one in the table below. An average molecular weight from about 600 to about 8,500 is preferred and can be obtained without optimization.

| | FDXL[a] | | | | | $T_D$[c] (°C.) | |
|---|---|---|---|---|---|---|---|
| Polymer | Isomers | $\bar{M}_n$[b] | $\bar{M}_w$[b] | $\bar{M}_w/\bar{M}_n$[b] | $T_G$ (°C.) | $N_2$ | Air |
| —FDXL—SiMe$_2$(OSiMe$_2$)$_2$— | (t) | 746 | 3,230 | 4.3 | −61 | 228 | 227 |
| —FDXL—SiMe$_2$OSiMe$_2$— | (t) | 1,090 | 1,730 | 1.6 | −59 | 170 | 180 |
| | (t/c) | 2,040 | 7,520 | 3.7 | −39 | 246 | 233 |
| —FDXL—SiMe(OSiMe$_3$)OSiMe(OSiMe)$_3$— | (t) | 2,400 | 5,930 | 2.5 | −44 | 263 | 265 |

-continued

| Polymer | FDXL[a] Isomers | $\bar{M}_n$[b] | $\bar{M}_w$[b] | $\bar{M}_w/\bar{M}_n$[b] | $T_G$ (°C.) | $T_D$[c] (°C.) N$_2$ | Air |
|---|---|---|---|---|---|---|---|
| —FDXL—SiMePhOSiMePh— | (t) | 1,430 | 2.270 | 1.6 | −27 | 233 | 241 |
| | (t/c) | 2,090 | 3.900 | 1.9 | −9 | 300 | 297 |
| | (c) | 1.320 | 2.080 | 1.6 | −15 | 244 | 238 |

[a]2,2-Bis(trifluoromethyl)-4,5-difluoro-4,5-divinyl-1,3-dioxolane (FDXL) isomers: t = trans, c = cis, t/c = trans/cis
[b]GPC vs. PS (Gas Permeation Chromatography vs. polystyrene standard) $M_n$ = average number of monomer units; $M_w$ = average molecular weight of units
[c]Temperature corresponding to 10% weight loss at 20° C./min heating rate The 2:1 adducts of formula IA are useful as additives to polymers, lubricants, primers, surface modifying agents and can be used with dissolved fluoropolymers to form coatings exhibiting low surface energy and improved abrasion resistance.

The oligomers and polymers of formula I are useful as low temperature lubricants and as substrates for low surface energy coatings.

EXAMPLES

GENERAL PROCEDURES

All preparations were carried out in a Vacuum Atmospheres Co. dry box or under nitrogen. In the examples that follow, commercial reagents were distilled prior to use when necessary. Trichlorosilane, 1,1,3,3-tetramethyldisiloxane, 1,3-diphenyl-1,3-dimethyldisiloxane, 2,2,2-trifluoroethanol, 1H, 1H-heptafluoro-1-butanol and d-limonene were purchased from Aldrich Chemical Co, Milwaukee, Wis., United Technologies Inc., Bristol, Pa., or PCR Inc., Gainesville, Fla. $HSi(OCH_2CF_3)_3$, and $HSi(OCH_2C_3F_7)_3$ were synthesized by slight modifications of published procedures. Platinum divinylsiloxane complex (3–3.5% Pt concentration in xylene, PC072) was obtained from United Technologies Inc., Bristol, Pa. and diluted 5:1 by volume (toluene, Pt complex) prior to use. $Co_2(CO)_8$ was obtained from Strem Chemicals Inc., Newburyport, Mass. Toluene was reagent grade and purified by distillation from calcium hydride prior to use. Perfluoro-2,2-dimethyl-1,3-dioxole was obtained pure from an internal DuPont source. Proton and carbon NMR were determined in deuterobenzene solvent on a GE model QE-300 instrument. The mass specroscopy experiments were performed on a Finnigan 4615B GC/MS quadrupole mass spectrometer (San Jose, Calif.). An electron impact source configuration operating at 200° C. and a source pressure of $1.0 \times 10^{-6}$ Torr was used. The mass spectrometer was scanned at a rate of about 1000 Daltons/second. All mass spectral peaks are recorded as sum of the ion plus potassium (M+ 39). $[CH_3CH(OH)CH_2]_2$—N $(CH_2C_6H5)(C_{12}H_{25})Cl$ (60% w/w aqueous solution obtained from E. I. du Pont de Nemours and Company) was used as the phase transfer catalyst. Gas chromatography was done using a Hewlett-Packard 5890 instrument with thermal conductivity detector using 15 m×0.53 mm DB-1 100% methyl silicone or DB-210 50% trifluoropropyl, 50% methyl silicone capillary column operating at 40°–250° C.

Gel permeation chromatography analyses were run on a Waters instrument (Model 590 pump) equipped with microstyragel columns (100, 500, $10^4$, $10^5$), and a refractive index detector, using THF solvent and polystyrene standards.

Thermogravimetric analysis (TGA) and differential scanning calorimetry (DSC) analyses were run on DuPont Instruments: 951 Thermogravimetric Analyzer and 912 Differential Scanning Calorimeter, respectively. Standard heating rate 20° C./min. were employed in a nitrogen or air, with samples of 5–30 mg.

Experiments 1–3 show a process for the synthesis of bis-2,2-trifluoromethyl-4,5-difluoro-4,5-divinyl-1,3-dioxolane, a starting material used to prepare the novel compounds of the present invention. (A process for the preparation of the starting material dioxolane is also described in U.S. Pat. Nos. 5,233,058 and 5,286,825 incorporated by reference herein.)

Experiment 1

Preparation of 2,2-bis(trifluoromethyl)-4,5-difluoro-4,5-diiodo-1,3-dioxolane

Perfluoro-2,2-dimethyl-1,3-dioxole (48.8 g, 0.2 mole) (U.S. Pat. No. 3,865,845 incorporated by reference herein) was mixed with iodine (70 g, 0.276 mole) in tetrahydrofuran solvent (20 ml) in a dried round-bottom flask. The reaction mixture was heated up slowly to 70° C. The reaction was monitored by gas chromatography and stopped when the conversion of the substrate reached completion. The product was distilled out from the reaction mixture, washed with saturated sodium thiosulfate aqueous solution and distilled again to give the desired product 69.4 g (70% yield) as a clear liquid, bp. 70° C./40–50 mm Hg. This product is a trans/cis isomeric mixture. $^{19}F$ NMR(Neat): −26.8 (m, trans); −39.5 (m, cis).

Experiment 2

Preparation of 2,2-bis(trifluoromethyl)-4,5-difluoro-4,5-di(2-iodoethyl)-1,3-dioxolane In a 400 ml stainless steel shaker tube was charged 2,2-bis(trifluoromethyl-4,5-difluoro-4,5-diiodo-1,3-dioxolane (199.2 g, 0.4 mole) and d-limonene (2.0 g). The tube was sealed, cool-evacuated and charged with ethylene (60 g, 2.14 mole). The tube was sealed and heated at 220° C. for 10 hrs. The tube was then cooled and the product mixture was fractionally distilled to give the desired product (115 g, 52% yield) as a pale yellow viscous liquid, bp. 105° C./0.5 mm Hg. The product was obtained as a trans/cis isomeric mixture. $^{19}F$ NMR (Neat): −79.0 (m, 6F); [−105.8 (m, trans); −108.0 (m, br, cis)] (2F total).

Experiment 3

Preparation of 2,2-bis(trifluoromethyl)-4,5-difluoro-4,5-divinyl-1,3-dioxolane

In a flask was charged 2,2-bis(trifluoromethyl)-4,5-difluoro-4,5-di(2-iodoethyl)-1,3-dioxolane (95 g, 017 mole), KOH (189 ml 10M, 1.89 mole) and phase transfer catalyst (Note) (24.6 g as 60% w/w aqueous solution, 0.034 mole).

The reaction mixture was vigorously stirred at ambient temperature for 4 hrs. The bottom organic layer was separated and was further purified by distillation giving 25.0 g (49.3% yield) of the desired product obtained as a clear, colorless liquid, bp. 90° C./200 mm Hg. This product is a trans/cis isomeric mixture. The trans and cis isomers could be separated by distillation on a spinning-band column. $^1$H NMR (CDCl$_3$): δ 5.90 (m, 2H), 5.70 (m, 4H) (trans isomer); 5.76 (m, 4H), 5.58 (m, 2H) (cis isomer); $^{19}$F NMR (CDCl$_3$): –80.2 (m, 6F), –109.6 (m, 2F) (trans isomer); –80.2 (m, 3F), –81.0 (q, J=8.6 Hz, 3F), –109.3 (quintet, J=7.0 Hz, 2F).

Examples 1–4 show the synthesis of certain novel compounds IA of the present invention. In particular Examples 1 and 2 combined show the route to a compound of the present invention wherein the R's of the silicon hydride are halogen. Example 3 and Example 4 show the process of the present invention to produce a novel compound of the present invention where the R's of the silicon hydride are not halogen.

Example 1

Synthesis of 2.2-bis(trifluoromethyl)-4,5-difluoro-4,5-bis(trichlorosilylethyl)-1,3-dioxolane A solution consisting of 4.018 g (13.5 mmol) of 2,2-bis(trifluoromethyl)-4,5-difluoro-4,5-divinyl-1,3-dioxolane as prepared above, 4.22 mL (41.8 mmol) of HSiCl$_3$ and three drops of Pt catalyst was placed in a pressure vessel and heated to 120° C. for 6 hr. After cooling, the volatiles were removed in vacuo leaving 3.56 g (47%) of a light brown tinted liquid identified as 2,2-bis(trifluoromethyl)-4,5-difluoro-4,5-bis(trichlorosilylethyl)-1,3-dioxolane. $^1$H NMR (C$_6$D$_6$) 1.1–1.3 (m, 2H, SiCH$_2$), 1.7–1.9 (m, 1H, CHCF), 1.95–2.2 (m, 1H, CHCF). $^{13}$C NMR(C$_6$D$_6$) 16.8 (s, CH$_2$Si), 26.3 (d, CHCF, $^2$J$_{(CF)}$=14 Hz), 26.4 (d, CHCF, $^2$J$_{(CF)}$=14 Hz), 119 (q, CF$_3$), 120 (d, CF).

Example 2

Synthesis of 2,2-bis(trifluoromethyl)-4,5-difluoro-4,5-bis(triethoxysilylethyl)-1,3-dioxolane A solution consisting of 3.00 g (5.28 mmol) of 2,2-bis(trifluoromethyl)-4,5-difluoro-4,5-bis(trichlorosilylethyl)-1,3-dioxolane, as prepared in Example 1, in 30 mL of heptane was heated to 70° C. Ethanol (2.80 mL, 47.7 mmol) was slowly added dropwise over a period of 15 min. Throughout the addition, HCl gas was vented by continuous bubbling of Ar through the solution. After stirring for 30 min, the reaction was cooled, and the volatiles were removed in vacuo leaving 2.90 g (88%) of a liquid identified as 2,2-bis(trifluoromethyl)-4,5-difluoro-4,5-bis(trichlorosilylethyl)-1,3-dioxolane by NMR. $^{13}$C NMR(C$_6$D$_6$) 3.54 (CH$_2$Si), 18.79 (CH$_3$), 27.45 (CHCF), 27.9 (CHCF), 59.09 (OCH$_2$), 110–130 (CF, CF$_3$). MS (m/e) 665 (M+39, 100%).

Example 3

Synthesis of 2,2-bis(trifluoromethyl)-4,5-difluoro-4,5-bis(tris(2,2,2-trifluoroethoxy)silylethyl)-1,3-dioxolane A mixture consisting of 0.503 g (1.69 mmol) of trans-divinyl-4,5-difluoro-1,3-dioxolane, as prepared above, 1.10 g (3.38 mmol) of HSi(OCH$_2$CF$_3$)$_3$ and 10 microliters of Pt catalyst was heated to 70° C. for 4 hr, cooled and stirred at room temperature for 16 hr. The excess silane was removed by vacuum leaving 1.19 g (73%) of 2,2-bis(trifluoromethyl)-4,5-difluoro-4,5-bis(tris(2,2,2-trifluoroethoxy)silylethyl)-1,3-dioxolane $^1$H NMR (C$_6$D$_6$) 1.18, ("t", SiCH$_2$) 2.1–2.3 (m, CH$_2$CF), 4.30 (q, CH$_2$CF$_3$). $^{13}$C NMR(C$_6$D$_6$) 2.26 (s, CH$_2$Si), ~25 (CH$_2$CF, obscured by solvent) 61.96 (q, OCH$_2$CF$_3$, $^2$J(CF)=36.4 Hz), 120 (m, CF), 124.97 (q, CF$_3$, $^1$J(CF)=277.6 Hz).

Example 4

Synthesis of 2,2-bis(trifluoromethyl)-4,5-difluoro-4,5-bis(tris(1H,1H-heptafluorobutoxy)silylethyl)-1,3-dioxolane A mixture consisting of 0.504 g (1.69 mmol) of trans-divinyl-4,5-difluoro-1,3-dioxolane, 2.10 g (3.36 mmol) of HSi(OCH$_2$(CF$_2$)$_2$CF$_3$)$_3$ and 10 µL of Pt catalyst was heated to 70° C. for 4 hr and cooled. NMR showed some unreacted vinyl groups so the mixture was heated to 85° C. for an additional 4 hr. Most of the excess silane was removed by vacuum leaving 1.40 g (53.4%) of 2,2-bis(trifluoromethyl)-4,5-difluoro-4,5-bis(tris(1H,1H-heptafluorobutoxy)silylethyl)-1,3-dioxolane. $^1$H NMR (THF-d$_8$) 1.1–1.3, (m, SiCH$_2$) 2.1–2.3 (m, CH$_2$CF), 4.48 (t, CH$_2$CF$_2$). $^{13}$C NMR (THF-d$_8$) 2.37 (s, CH$_2$Si), ~25 (CH$_2$CF, obscured by solvent) 61.62 (t, OCH$_2$CF$_2$, $^2$J$_{(CF)}$=27.6 Hz), 105–124 (m, CF, CF$_3$).

Examples 5–6 show the preparation of compounds I of the present invention wherein x>1.

Example 5

Preparation of (trans-2,2-bis(trifluoromethyl)-4,5-difluoro-4,5-divinyl-1,3-dioxolane-HSi(CH$_3$)$_2$OSi(CH$_3$)$_2$H copolymer)

Co$_2$(CO)$_8$ (0.05 g, 0.145 mmol) was stirred into a mixture of trans-2,2-bis(trifluoromethyl)-4,5-difluoro-4,5-divinyl-1,3-dioxolane (0.5 g, 1.68 mmol) and 1,1,3,3-tetramethyldisiloxane (0.23 g, 1.71 mmol). After 1.5 hr, $^1$H NMR showed complete SiH conversion, 5% of the unreacted divinyl dioxolane and 70% of the desired product. After 24 hr the reaction mixture was diluted with CCl$_2$FCClF$_2$, washed with methanol and water, and volatiles stripped on a rotary evaporator and under high vacuum. Yield: 0.4 g (55%), very viscous liquid. $^1$H NMR (THF-d$_8$): δ0.2 (br m, 6H), 0.9 (br t, 4H), 2.0–2.2 (br m, 4H); $^{19}$F NMR (THF-d$_8$+"FREON" 11): –80.0 (m, 6F), –110.8 (m, 2F), –108.0, –111.7 (minor); GPC (vs PS): M$_n$=1,090, M$_w$=1,730, M$_w$/M$_n$=1.6, DSC: T$_G$=–59° C.

Example 6

Preparation of (trans-2,2-bis(trifluoromethyl)-4,5-difluoro-4,5-divinyl-1,3-dioxolane-HSi(CH$_3$)(C$_6$H$_5$)OSi(CH$_3$)(C$_6$H$_5$)H copolymer)

This material was prepared from trans-2,2-bis(trifluoromethyl)-4,5-difluoro-4,5-divinyl-1,3-dioxolane (0.5 g, 1.68 mmol), 1,3-diphenyl-1,3-dimethyldisiloxane (0.43 g, 1.66 mmol) and Co$_2$(CO)$_8$ (0.05 g, 0.145 mmol) as described for Example 5. $^1$H NMR showed 72% of the desired product. Yield: 0.5 g (54%), very viscous liquid. $^1$H NMR (THF-d$_8$): δ0.4 (br m, 6H), 1.0 (br m, 4H), 2.0 (br m, 4H), 7.2–7.6 (br, m, 10H); $^{19}$F NMR (THF-d$_8$+"FREON" 11): –80.05 (m, 6F), –110.7 (m, 2F), –79.7, –107.8, –111.6 (minor); GPC (vs PS): M$_n$=1,430, M$_w$=2,270, M$_w$/M$_n$=1.6, DSC: T$_G$=–27° C.

What is claimed is:

1. A polymer, comprising repeat units of formula I

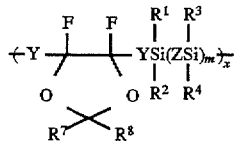

wherein:
- x is an integer from 2 to 100;
- m is an integer from 1 to 50;
- $R^1$, $R^2$, $R^3$ and $R^4$ are each independently $C_1$ to $C_{20}$ alkyl, aryl, cycloalkyl, halogen, $C_1$ to $C_{20}$ alkoxy, $C_2$ to $C_{20}$ fluoroalkoxy, trifluoropropyl, aryloxy, $C_1$ to $C_{20}$ acyloxy, oxysilyl or hydrogen;
- Z is a divalent group selected from the group consisting of: O, S, and $R^6N$;
- $R^6$ is $C_1$ to about $C_8$ alkyl;
- $R^7$ and $R^8$ are each independently $C_1$ to $C_8$ fluoroalkyl or fluorine;
- Y is $(CR^9R^{10})_kCR^{11}HCR^{13}R^{14}$;
- $R^9$, $R^{10}$, $R^{11}$, $R^{13}$ and $R^{14}$ are each independently hydrogen, $C_1$ to about $C_8$ alkyl or aryl; and
- k is an integer from 0 to 10.

2. The polymer of claim 1 wherein Z is selected from the group consisting of O or S.

3. The polymer of claim 1 wherein m is 1 to 3.

4. The polymer of claim 1 wherein $R^1$, $R^2$, $R^3$ and $R^4$ are $C_1$ to $C_4$ alkyl, $C_1$ to $C_4$ alkoxy, $C_2$ to $C_4$ fluoroalkoxy or chlorine.

5. A process for the preparation of a polymer comprising repeat units of formula I

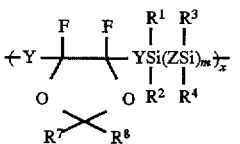

wherein:
- x is an integer from 2 to 100;
- m is an integer from 1 to 50;
- $R^1$, $R^2$, $R^3$ and $R^4$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, oxysilyl or hydrogen;
- Z is a divalent group selected from the group consisting of: O, S, and $R^6N$;
- $R^6$ is $C_1$ to about $C_8$ alkyl;
- $R^7$ and $R^8$ are each independently $C_1$ to $C_8$ fluoroalkyl or fluorine;
- Y is $(CR^9R^{10})_kCR^{11}HCR^{13}R^{14}$;
- $R^9$, $R^{10}$, $R^{11}$, $R^{13}$ and $R^{14}$ are each independently hydrogen, $C_1$ to about $C_8$ alkyl or aryl; and
- k is an integer from 0 to 10, comprising, contacting a silicon hydride of formula II

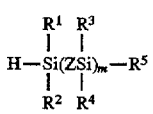

wherein
$R^5$ is $C_1$ to $C_{20}$ alkyl, aryl, vinyl or hydrogen and m, Z, $R^1$, $R^2$, $R^3$ and $R^4$ are as defined for formula I, with a divinyl dioxolane of formula III

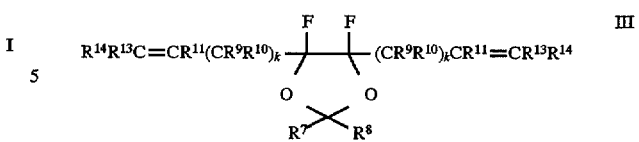

wherein
$R^7$, $R^8$, $R^9$, $R^{10}$, $R^{11}$, $R^{13}$, $R^{14}$ and k are as defined for formula I, in the presence of a transition metal catalyst to form a polymer comprising repeat units of formula I.

6. The process of claim 5 wherein for the silicon hydride $R^1$, $R^2$, $R^3$, $R^4$ and $R^5$ are $C_1$ to $C_4$ alkyl, $C_1$ to $C_4$ alkoxy, or oxysilyl.

7. The process of claim 5 wherein the silicon hydride is selected from the group consisting of: 1,1,3,3-tetramethyldisiloxane; 1,3-diphenyl-1,3-dimethyldisiloxane, $HSi(CH_3)_2OSi(CH_3)_2OSi(CH_3)_2H$; and $HSi(CH_3)(OSi(CH_3)_3)OSi(CH_3)(OSi(CH_3)_3)H$.

8. The process of claim 5 wherein the catalyst is $Co_2(CO)_8$ and $Co_2(CO)_{8-z}L_z$, wherein z is 0 or an integer of 1 to 7, each L is independently Co, $PR^{20}_3$ or $P(OR^{21})_3$; $R^{20}$ is hydrocarbyl; $R^{21}$ is hydrocarbyl; and provided that when L is $PR^{20}_3$ only one or two of $R^{20}$ is aryl.

9. A compound of formula IA

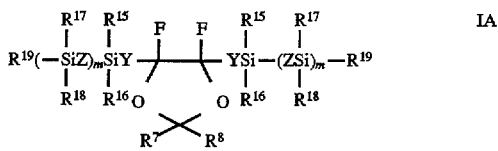

wherein:
- m is an integer from 0 to 50;
- $R^{15}$, $R^{16}$, $R^{17}$ and $R^{18}$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, $C_1$ to $C_{14}$ fluorocarboxy; oxysilyl or hydrogen;
- $R^{19}$ is $C_1$ to $C_{20}$ alkyl, aryl, $C_1$ to $C_{20}$ alkoxy, $C_2$ to $C_{20}$ fluoroalkoxy, $C_1$ to $C_{20}$ carboxy, $C_1$ to $C_{14}$ fluorocarboxy, halogen, vinyl or hydrogen;
- Z is a divalent group selected from the group consisting of: O, S, and $R^6N$;
- $R^6$ is $C_1$ to about $C_8$ alkyl;
- $R^7$ and $R^8$ are each independently $C_1$ to $C_8$ fluoroalkyl or fluorine;
- Y is $(CR^9R^{10})_kCR^{11}HCR^{13}R^{14}$;
- $R^9$, $R^{10}$, $R^{11}$, $R^{13}$ and $R^{14}$ are each independently hydrogen, $C_1$ to about $C_8$ alkyl or aryl; and
- k is an integer from 0 to 10.

10. The compound of claim 9 wherein m is 0.

11. The compound of claim 9 wherein $R^{15}$, $R^{16}$, $R^{17}$, $R^{18}$ and $R^{19}$ are independently selected from the group consisting of: $C_1$ to $C_4$ alkyl, aryl, $C_1$ to $C_4$ alkoxy, $C_1$ to $C_6$ acyloxy, $C_1$ to $C_4$ fluorocarboxy, chlorine or bromine.

12. The compound of claim 9 wherein $R^9$, $R^{10}$, $R^{11}$, $R^{13}$ and $R^{14}$ are hydrogen.

13. The compound of claim 9 selected from the group consisting of: 2,2-bis(trifluoromethyl)-4,5-difluoro-4,5 bis(trichlorosilylethyl)-1,3-dioxolane; 2,2-bis(trifluoromethyl)-4,5-difluoro-4,5 bis(triethoxysilylethyl)-1,3-dioxolane; 2,2-bis(trifluoromethyl)-4,5-difluoro-4,5 bis(tris(2,2,-trifluoroethoxy)silylethyl)-1,3-dioxolane; and 2,2-bis(trifluoromethyl)-4,5-difluoro-4,5 bis(tris(1H,1H-heptafluorobutoxy)silylethyl)-1,3-dioxolane.

14. A process for preparing a compound of formula IA

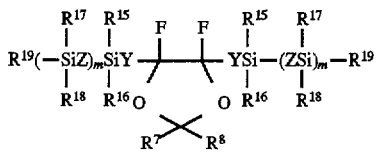

wherein:

m is an integer from 0 to 50;

$R^{15}$, $R^{16}$, $R^{17}$ and $R^{18}$ are each independently $C_1$ to $C_{20}$ alkyl, aryl, cycloalkyl, halogen, $C_1$ to $C_{20}$ alkoxy, $C_2$ to $C_{20}$ fluoroalkoxy, aryloxy, $C_1$ to $C_{20}$ acyloxy, $C_1$ to $C_{14}$ fluorocarboxy, oxysilyl or hydrogen;

$R^{19}$ is $C_1$ to $C_{20}$ alkyl, aryl, $C_1$ to $C_{20}$ alkoxy, $C_2$ to $C_{20}$ fluoroalkoxy, $C_1$ to $C_{20}$ carboxy, $C_1$ to $C_{14}$ fluorocarboxy, halogen, vinyl or hydrogen;

Z is a divalent group selected from the group consisting of: O, S, and $R^6N$;

$R^6$ is $C_1$ to about $C_8$ alkyl;

$R^7$ and $R^8$ are each independently $C_1$ to $C_8$ fluoroalkyl or fluorine;

Y is $(CR^9R^{10})_kCR^{11}HCR^{13}R^{14}$;

$R^9$, $R^{10}$, $R^{11}$, $R^{13}$ and $R^{14}$ are each independently hydrogen, $C_1$ to about $C_8$ alkyl or aryl; and k is an integer from 0 to 10, comprising: contacting a silicon hydride of formula IIA

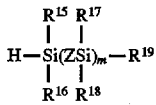

wherein m, Z, $R^{15}$, $R^{16}$, $R^{17}$, $R^{18}$ and $R^{19}$ are as defined for formula IA, with a divinyl dioxolane of formula III

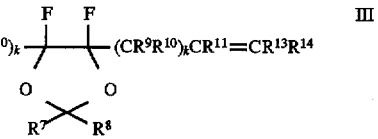

wherein $R^7$, $R^8$, $R^9$, $R^{10}$, $R^{11}$, $R^{13}$, $R^{14}$ and k are as defined for formula IA, in the presence of a transition metal catalyst to form a compound of formula IA.

15. The process of claim 14 wherein contact is made in the presence of a solvent.

16. The process of claim 14 wherein the silicon hydride has the formula $R_aSiH_{4-a}$ wherein each R is independently $C_1$ to $C_4$ alkyl; aryl; chlorine; bromine; $C_1$ to $C_4$ alkoxy, $C_1$ to $C_4$ fluoroalkoxy; $C_1$ to $C_4$ fluorocarboxy; or acyloxy containing 1 to 6 carbon atoms, and a is 3.

17. The process of claim 14 wherein $R^9$, $R^{10}$, $R^{11}$, $R^{13}$ and $R^{14}$ are hydrogen.

18. The process of claim 14 wherein for the silicon hydride m is 0 and $R^{15}$, $R^{16}$ and $R^{19}$ are halogen, further comprising subsequently contacting the compound of formula IA with an alcohol or a fluoroalcohol to form a second compound of formula IA.

* * * * *